United States Patent [19]
Anderson et al.

[11] Patent Number: 5,556,612
[45] Date of Patent: Sep. 17, 1996

[54] METHODS FOR PHOTOTHERAPEUTIC TREATMENT OF PROLIFERATIVE SKIN DISEASES

[75] Inventors: R. Rox Anderson, Lexington, Mass.; Luciann Hruza, St. Louis, Mo.; Nikiforos Kollias, Belmont, Mass.

[73] Assignee: The General Hospital Corporation, Boston, Mass.

[21] Appl. No.: 213,126

[22] Filed: Mar. 15, 1994

[51] Int. Cl.$^6$ ............................... A61K 7/40; A61K 7/42
[52] U.S. Cl. .............................................. 424/59; 514/863
[58] Field of Search .................................................. 424/59

[56] References Cited

U.S. PATENT DOCUMENTS

| | | | |
|---|---|---|---|
| 2,949,403 | 8/1960 | Andreadis et al. | 167/90 |
| 4,325,965 | 4/1982 | Chiba | 514/863 |
| 4,454,159 | 6/1984 | Musher | 514/438 |
| 4,651,739 | 3/1987 | Oseroff et al. | 128/395 |
| 4,981,681 | 1/1991 | Tosti | 424/78 |
| 5,112,613 | 5/1992 | Honda et al. | 424/400 |
| 5,122,536 | 6/1992 | Perricone | 514/474 |
| 5,126,135 | 6/1992 | Yamada et al. | 424/401 |

FOREIGN PATENT DOCUMENTS

| | | | |
|---|---|---|---|
| 245149 | 9/1960 | Australia | 424/59 |

OTHER PUBLICATIONS

Fowlks, The Journal of Investigative Dermatology, 1959, vol. 32, "The Chemistry of Psoralens" pp. 249–254.
Pathak et al, The Jounal of Investigative Dermatology, 1959, vol. 32, pp. 255–262.
Follett et al., "Protection of Photosensitized Rats against Long Ultraviolet Radiation by Topical Application of Compounds with Structures Similar . . . Dihydroxyacetone" Dermatologica, 175:58–63 (1987).
Levy et al., "Dihydroxyacetone–containing sunless or self--tanning lotions" J. Amer. Acad. of Dermatology, 27:989–993 (1992).
Lui et al., "Photodynamic Therapy in Dermatology" Arch. Dermatol., 128:1631–1636 (1992).
Maibach et al., "Dihydroxyacetone: A Suntan–Simulating Agent" Archives of Dermatology, pp. 505–507, (1960).
Takahashi et al., "Measurement of turnover time of stratum corneum using dansyl chloride flourescence" J. Soc. Cosmet. Chem., 38:321–331 (1987).
Weinstein et al., "Low Dose Photofrin II Photodynamic Therapy of Psoriasis" Clinical Research, 39:509A (1991).
Weinstein et al., "Cell Kinetic Basis for Pathophysiology of Psoriasis" J. Investigative Dermatology, 55:579–583, (1985).
Kawada, A. et al., Acta Derm. Venereol., vol. 69, pp. 335–337 (1989).
Van Praag, M. C. G. et al., J. Invest. Derm., vol. 97(4), pp. 629–633 (1991).
Rippke, F. et al., Puva Therapy of Psoriasis, vol. 69(10), pp. 671–676 (1994).
Fitzpatrick et al., "Historical Aspects of Methoxsalen and Other Furocoumarins," J. of Investigative Dermatology, 32:229–231, 1959.
Fowlks et al., "The Mechanism of the Photodynamic Effect," J. of Investigative Dermatology, 32:233–243, 1959.
Stegmaier, "The Use of Methoxsalen in Sun Tanning," J. of Investigative Dermatology 32:345–349, 1959.
PCT International Search Report for PCT/US95/03130 (mailed Jun. 15, 1995).

*Primary Examiner*—Shelley A. Dodson
*Attorney, Agent, or Firm*—Fish & Richardson P.C.

[57] ABSTRACT

Method for treating a proliferative skin disorder, such as psoriasis, in a human patient having affected and non-affected areas of skin. The method comprises the steps of: (1) topically applying a sunscreen providing photo-protection to the affected and non-affected areas of skin; (2) waiting for a time period sufficient for the skin of the affected areas to be substantially sloughed off; and, (3) exposing the affected and non-affected areas of skin of the patient to a selected level of optical radiation. The level of radiation is chosen to be sufficient to treat the affected areas of skin and insufficient to cause significant damage to the non-affected areas of skin. The method enhances effectiveness and safety of treatment by providing preferential photo-protection to the non-affected skin areas, and may be used for phototherapy, photochemotherapy, or photodynamic therapy.

15 Claims, 4 Drawing Sheets

METHODS FOR PHOTOTHERAPEUTIC TREATMENT OF PROLIFERATIVE SKIN DISEASES

This invention was made with Government support under Contract #RO1 AR25395 awarded by the National Institutes of Health. The Government has certain rights in the invention.

FIELD OF THE INVENTION

This invention relates to treatment of psoriasis and other proliferative skin diseases using phototherapeutic techniques.

BACKGROUND OF THE INVENTION

Proliferative skin diseases, such as psoriasis, eczema, mycosis fungoides, actinic keratosis, and lichen planus, are known to effect one to two percent of the U.S. population, with as many as 150,000–260,000 new cases occurring annually ("Research Needs in 11 Major Areas in Dermatology" I. Psoriasis. *J. Invest. Dermatol.* 73:402–13, 1979). One method used to treat the rapid proliferation of skin cells is phototherapy, which utilizes optical absorption of ultraviolet (UV) radiation by the skin to kill rapidly growing cells and arrest proliferation. At present, both UVA and UVB therapy, which expose the skin to UV radiation between 320–400 nm (UVA radiation) or 290–320 nm (UVB radiation), are effective and widely used. PUVA therapy, a form of photochemotherapy which involves repeated topical application of psoralen or a psoralen-based compound to an affected region of skin, followed by exposure of that region to UVA radiation, is also widely used. Another method used to treat proliferative skin diseases, particularly psoriasis and mycosis fungoides, is photodynamic therapy (PDT). In this method, a photosensitizing agent, which is a drug selectively retained in carcinoma cells, is administered to a patient. Following absorption of light (typically between 320–700 nm, depending on the drug) the photosensitizing agent undergoes a photochemical reaction, resulting in the production of cytotoxic singlet oxygen which eventually leads to tumor vessel destruction in the skin (Anderson, et al., *Arch. Dermatol.* 128:1631–1636, 1992).

Prolonged treatment for proliferative skin diseases using these types of therapies can, however, result in significant acute and chronic adverse effects including erythema, pruritus, skin cancer, and chronic light-induced damage of the skin (Stern et al., *N.E. J. Med.* 300:809–812, 1979).

It is therefore desirable to reduce the number of times the skin is exposed to radiation during phototherapy. PUVA therapy (Wolff, Pharmacol. Ther. 12:381, 1981), and frequent alternation of PUVA therapy with other treatments (Parris et al., *The Science of Photomedicine*, Regan et al., eds., 1982, p. 615) have been suggested as methods to reduce the cumulative number of iterations (typically around 25) required for successful treatment. Another method used to decrease the number of phototherapy treatments involves increasing the optical fluence during therapy (Honigsmann et al., *Dermatology in General Medicines*, 3rd ed, T. B. Fitzpatrick et al., eds., 1533–1558, 1987; Ryatt, et al., *J. Am. Acad. Dermatol.* 9:558–562, 1983). Up to a threefold reduction in the time required for the affected region to clear is possible when isolated plaques are exposed to radiation levels between two and three times the minimal erythema dose (MED), defined as the level of optical fluence resulting in the onset of erythema (Parrish et al., *J. Invest. Dermatol.* 76:359–362, 1981).

Because both UVA and UVB radiation are harmful to normal skin, the tolerable limit of treatment aggressiveness is ultimately limited by adverse effects resulting from the cumulative exposure of the skin to UV radiation. Presently, the level of UV radiation is kept as high as possible during phototherapeutic treatments, just less than the level causing painful sunburn.

In order to reduce the effects of increased exposure to UV radiation during phototherapy, it is possible, but impractical, to apply sunscreens to all the non-affected skin areas which surround sites of affected skin; most proliferative skin diseases involve tens or hundreds of affected regions which are randomly located over the body. In addition, during PDT there is often appreciable uptake of the photosensitizing agent in the non-affected regions of skin, making it desirable to protect these regions from drug-activating radiation.

SUMMARY OF THE INVENTION

The present invention features, in general, a method for treating a proliferative skin disorder in a human patient having affected and non-affected areas of skin. The term "proliferative skin disorder", as used herein, refers to psoriasis, eczema, actinic keratosis, mycosis fungoides, lichen planus, and other diseases resulting in rapid proliferation of skin cells.

The method of the present invention features the steps of: (a) topically applying a sunscreen providing photo-protection to the affected and non-affected areas of skin; (b) waiting for a time period sufficient for the skin of the affected areas to be sloughed off to a greater degree than skin of non-affected areas; and, (c) exposing the affected and non-affected areas of skin of the patient to a selected level of optical radiation sufficient to treat the affected areas of skin and insufficient to cause significant damage to the non-affected areas of skin.

One essential feature of proliferative skin disorders that is used to advantage in the method of the present invention is that of hyper-proliferation of the epidermis, the outer layer of skin. Affected regions of skin grow and are sloughed off at a rate of about ten times than that of non-affected regions. A topically-applied substance, such as a sunscreen, adhering to the stratum corneum of the affected regions will therefore be sloughed off much faster relative to sunscreen applied to the non-affected regions. After a predetermined period of time, this results in the non-affected regions of skin retaining a large amount of sunscreen relative to the affected regions.

Preferably, between steps (b) and (c), the amount of photo-protection provided by the sunscreen to the affected and/or non-affected areas of the patient's skin is determined, e.g., using a non-invasive optical method involving measuring the reflectance properties of sunscreen-treated skin. In alternate embodiments, a photosensitizing agent, psoralen, or a psoralen-based compound is administered to the patient prior to step (c).

The sunscreen preferably contains an active compound, e.g. Dihydroxyacetone ("DHA"), which binds to portions of the stratum corneum to partially absorb optical radiation, most preferably in the spectral region between 290–400 nm. When a photosensitizing agent, psoralen, or a psoralen-based compound is administered to the patient, the optical absorption of the active compound is preferably in the spectral regime between 320–700 nm.

In preferred embodiments, the method of the present invention is used to treat psoriasis, mycosis fungoides, eczema, actinic keratosis, or lichen planus. Other features and advantages of the invention will be apparent from the following description of the preferred embodiments thereof, and from the claims.

DETAILED DESCRIPTION OF THE INVENTION

Sunscreens for Phototherapy

Figure 1:
FIG. 1 is a fluorescence microscopy photograph of a frozen sample of biopsied skin taken 1 day after being stained in vivo with DHA.

The sunscreens used during the phototherapeutic method of the invention contain an active compound which exhibits desirable chemical and optical properties. By desirable "chemical" properties is meant that the active compound must be of acceptable low toxicity and be able to adhere to both affected and non-affected regions of the skin. Furthermore, the active compound should be highly substantive, meaning that it is not easily washed off, and should adhere to elements of the stratum corneum (e.g., keratin, other proteins, lipids, etc.) preferably through covalent bonding.

By desirable "optical" properties is meant that, once adhered to the skin, the active compound should have a broad absorption spectrum in the UV and/or visible frequency range, and should have the ability to absorb at least 50% of the incident radiation, and preferably 80% or more. The active compound should also not undergo photodegradation following the absorption of light, and should minimize hyperpigmentation of the skin during the phototherapy. Active compounds exhibiting desirable chemical and optical properties which can be incorporated into a moisturizing base to form sunscreens according to the invention are listed in Table 1.

TABLE 1

Active Compounds for Sunscreens

| Compound | Concentration permitted (% by weight) | Absorbance range (nm) |
|---|---|---|
| Glycerylaminobenzoate | 3.0–5.0 | 260–315 |
| Amyl-p-dimethylamino benzoate (Padimate-A) | 1.0–5.0 | 290–315 |
| 2-Ethyl-hexyl-p-dimethylamino benzoate (Padimate-O) | 1.4–8.0 | 290–315 |
| 2-Ethoxyethylhexyl-p-methoxycinnamate (cinnoxate) | 1.0–3.0 | 270–328 |
| 2,2-Dihydroxy-4-methoxybenzo-phenone (dioxybenzone) | 3.0–5.0 | 260–380 |
| 2-Hydroxy-4-methoxybenzo-phenone (oxybenzone) | 2.0–6.0 | 270–350 |
| 2-Hydroxy-4-methoxybenzo-phenone 5-sulfonic acid (sulisobenzone) | 5.0–10.0 | 270–360 |
| 3,3,5-Trimethylcyclohexyl-salicylate (homosalate) | 4.0–15.0 | 290–315 |
| Dihydroxyacetone | 5.0–15.0 | 320–390 |

A preferred active compound is DHA (dihydroxyacetone). DHA is a colorless, naturally-occurring three carbon sugar (Lehninger, *Biochemistry*, Worth Publishers, New York, 1970) which has been used topically for the past three decades as the active ingredient in many popular "sunless tanning" products. When applied topically, DHA penetrates superficially into the stratum corneum where it covalently binds to epidermal proteins via their amino groups, producing a cosmetically-acceptable "tan" color which effectively photo-protects against visible light. DHA also exhibits strong absorption of near ultraviolet optical radiation, and is fluorescent following the absorption of radiation.

Therapy

The application of adherent sunscreens containing active compounds is followed by a period during which preferential loss of skin in the affected regions (i.e., the lesions) occurs because of rapid skin proliferation, leaving these regions with a lower concentration of the sunscreen relative to the non-affected regions. The affected regions of skin are thus left relatively unprotected from optical radiation during phototherapy or PDT. By selectively protecting the non-affected skin, the method of the present invention allows: (1) more aggressive phototherapies, leading to an acceleration of the skin clearing process (Carabott et al., *Clin. Exp. Dermatol.* 14:337–340, 1989); (2) reduction in the occurrence of sunburn, skin cancers, and other acute side effects; and, (3) a decrease in the number of treatments necessary for treating rapidly proliferating skin diseases, thus simplifying the therapy. The method of the present invention therefore makes treatment of affected skin using phototherapy, PDT or photochemotherapy both safer and more efficient.

Sunscreen Interaction with the Stratum Corneum

Following topical application, the sunscreens preferably bind to proteins contained in the top cell layers of the stratum corneum. Alternatively, they may polymerize or bind with other components of the skin, such as lipids. In the case of DHA, this results in the formation of an oxidized compound which exhibits fluorescent behavior following the absorption of light (Ellis *Adv. Carbohydrate Chem.* 14:63–135, 1959).

In order to determine the depth of staining, samples of psoriatic skin were treated with a single application of a 5%

Figure 1A:
FIG. 1a is a fluorescence microscopy photograph of a frozen sample of biopsied skin taken 3 days after being stained in vivo with DHA.
Figure 1B:
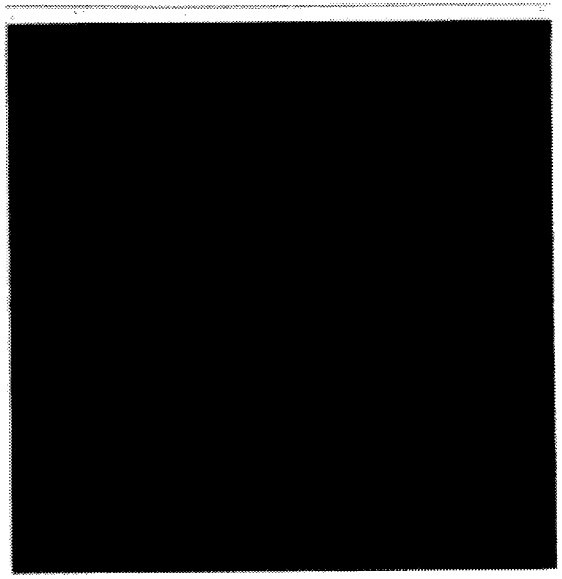
FIG. 1b is a fluorescence microscopy photograph of a frozen sample of unstained, biopsied skin.

(by weight) solution of DHA (0.2 cc/9 cm$^2$) and then biopsied. Frozen sections of skin were prepared, and the fluorescence of DHA as a function of depth in the skin was measured using standard spectroscopy techniques after 1- and 3-day periods. Referring now to FIGS. 1, 1a, and 1b, fluorescence induced in the DHA stained skin after a 1-day period was limited to the upper half of the stratum corneum. The intensity of the fluorescence was significantly reduced after a 3-day period due to sloughing off of the stratum corneum. The fluorescence intensity of the stained skin samples was compared with an unstained control sample in the study.

The depth of DHA penetration was also measured in a separate study by topically applying a solution of DHA, waiting a period of time sufficient for DHA to penetrate the stratum corneum, and finally peeling off layers of skin with an adhesive tape while measuring the intensity of the induced fluorescence.

Figure 2:
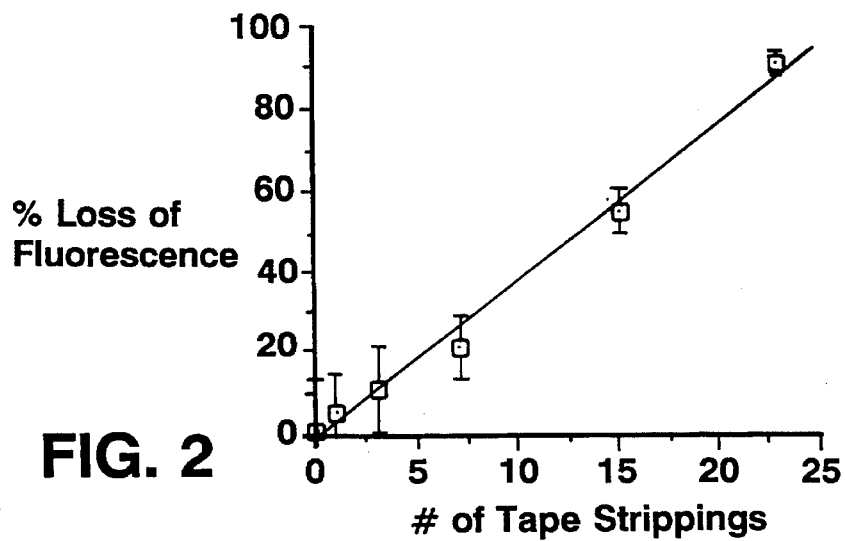
FIG. 2 is a graph showing the fluorescence intensity of a skin sample stained with DHA as a function of the number of tape strippings, each of which remove portions of the stratum corneum.

Using a topically-applied sunscreen, a thin layer of DHA was deposited on a section of the forearm of three normal volunteers. After allowing sufficient time for the DHA to diffuse into the stratum corneum (4–6 hours) an adhesive tape was applied to the skin in the region of the applied sunscreen. Peeling of the tape resulted in the removal of approximately one layer of skin cells having a thickness of about 0.5 µm. The fluorescence intensity of the resultant skin surface was measured non-invasively after stripping each skin layer using standard spectroscopy techniques. The process was repeated, with the induced fluorescence intensity due to the presence of DHA decreasing with each stripping. FIG. 2 illustrates the linear relationship between the removal of skin layers and loss of fluorescence intensity, indicating that following application, DHA diffuses into the skin and stains the upper corneocyte layers uniformly. Complete loss of fluorescence occurred after stripping away 25 layers of skin, equal to a depth of about 10–15 µm, which is approximately the thickness of the human stratum corneum.

The ideal concentration of active compounds in sunscreens produces a highly photo-protective layer that is bound just at the skin surface. Concentrations that are higher lead to excess amounts of the active compound binding within the stratum corneum, resulting in an increase in the time required for the active compound to be substantially shed, thus lengthening the time between sunscreen application and phototherapy. Although the stratum corneum of psoriatic skin is sloughed off at 8 times the rate of normal skin, it is also many times thicker. Therefore, active compounds which bind throughout the stratum corneum result in a higher level of staining, and may actually take longer to be completely sloughed off.

The desirable concentration of DHA or other active components in sunscreen is defined as that necessary to provide substantial photo-protection to normal skin. For DHA, this was determined by varying the DHA concentration and repeating the experiment described above, and was determined to be between 5–15% by weight. With different vehicles or agents which affect DHA staining of skin, lower concentrations may be used. Desirable concentrations of other active compounds in sunscreens are listed in Table 1.

Because both the concentration of stratum corneum binding sites and kinetics of sloughing are expected to change during the clearing phase of phototherapy, the concentration of the active compound may have to be selectively adjusted during treatment. Differential loss of the active compound from affected skin regions is typically marked in early treatments, but as the regions clear, the rate of loss decreases and the active compound is retained longer. Depending on the patient, the frequency of application and concentration of the active compound may therefore be changed during the course of phototherapy in accordance with the sloughing rates and binding site changes of the skin. It is a routine matter to make such frequency and concentration adjustments using the guidance given herein.

Alternatively, a photosensitizing agent, psoralen, or a psoralen-based compound may be administered to a patient and used in combination with a topically-applied sunscreen. The compounds may be administered in one of the traditional modes (e.g., orally, parenterally, transdermally or transmucosally), in a sustained-release formulation using a biodegradable, biocompatible polymer, or by on-site delivery using micelles, gels and liposomes. Once administered, a sufficient time period is allowed to pass in order for the compound to be selectively retained in affected skin regions. Preferably, the compound is administered so that the ratio of drug retained in the affected and non-affected regions is maximized at approximately the same time that the ratio of the amount of sunscreen covering these regions is minimized. This allows for efficient treatment of the affected regions of skin using PDT.

Examples of photosensitizing agents which can be used in the method of the present invention include hematoporphyrin derivative (HPD), porfimer sodium (Photofrin), benzoporphyrin-derivative monoacid ring A (BPD-MA), mono-1-aspartyl chlorin e6 (NPe6), chloroaluminum sulfonated phthalocyanine, and similar light-absorbing compounds which are selectively retained in affected skin regions and become activated (i.e., undergo photochemical reactions to produce cytotoxic singlet oxygen) following optical absorption. In addition, 5-aminolevulinic acid (ALA), a naturally-occurring precursor to the biosynthesized porphryin Protoporphyrin IX, may be used as a photosensitizing agent. Examples of psoralen-based compounds which can be used in the method of the present invention include 8-MOP (methoxsalen, xanthotoxin), 5-methoxypsoralen (5-MOP, bergaptin), 7-methylpyridopsoralen, isopsoralen, and other isomeric and chemical derivative forms of psoralen.

Determination of Optical Fluence Levels for Phototherapy

The minimal erythema dose (MED) is the fluence, measured as energy per unit area, of radiation necessary to produce delayed erythema in a patient after irradiation. After receiving a photosensitizing agent, the amount of radiation needed to produce delayed erythema is called the minimal phototoxic dose (MPD). The phototoxic protection factor (PPF) refers to the ability of a sunscreen to protect the skin from photosensitized skin reactions, and is defined as the ratio of the MEDs or MPDs for skin protected with and without a sunscreen. Thus, the PPF provided by a sunscreen for a certain skin type can be determined by exposing the skin to UV fluence high enough to induce erythema in treated and untreated skin regions, and then determining the ratio of the optical fluences.

Because the sunscreen acts as a passive optical attenuating filter, the PPF is also simply related to the transmittance of light through the stratum corneum of protected skin. Following application of a sunscreen, accurate determination of the PPF for a particular skin sample allows the appropriate light level to be selected for phototherapy. Overestimation of the PPF may result in burning of the skin during treatment, while underestimation may reduce the effectiveness of phototherapy, thus prolonging treatment.

The PPF of a skin sample can be accurately determined using a non-invasive technique involving measuring the diffuse component of reflectance from a patient's skin (Wan et al., *J. Photochem. Photobiol.* 34:493–499, 1981; Kollias et al., *Biological Responses to UVA Radiation*, F. Urbach, ed., Valdenmar Pub. Co., Overland Park, Kans., 1992). It was determined for DHA staining of skin that the PPF is approximately equal to the square root of the ratio of diffuse light reflected from the skin before and after application of a sunscreen. The PPF can be expressed by the equation:

$$PPF = \sqrt{R_o / R_{sunscreen}} \quad (1)$$

Where $R_o$ and $R_{sunscreen}$ are the diffuse reflectance components of skin before and after application of a sunscreen, respectively, at the wavelength of interest. This result can also be expressed logarithmically as $$\log PPF = \frac{1}{2}(OD_{sunscreen} - OD_o) = (\Delta OD)/2 \quad (2)$$

where OD is the apparent optical density of the skin defined conventionally as $$OD = \log R \quad (3)$$

where R is the diffuse reflectance at the wavelength of interest for photoprotection.

The PPF can therefore be measured by irradiating the surface of the skin with light having the appropriate wavelength, measuring the reflected light with a suitable photodetector, and then estimating the PPF using equation (1) above.

A sunscreen including an active compound provides a specific PPF for the skin, and may also stain the skin to a color depending on the skin type of the patient. These two factors can be compared for various skin types, and a "color chart" can be established which correlates the level of staining with the provided PPF. This allows approximation of the PPF by simple inspection of the level of skin staining, thus simplifying the procedure used to determine the appropriate level of optical radiation to be used during treatment.

Optical Irradiation of the Skin

Following the determination of the PPF and the appropriate level of optical irradiation, therapy may be conducted with standard treatment units well known in the art. For UVB phototherapy, sources emitting wavelengths less then 320 nm are used. For UVA and PUVA therapy, such units typically include fluorescent bulbs capable of emitting optical radiation peaked near 355 nm. The intensities of UVA doses are typically measured with photodetectors having maximum sensitivities between 350–360 nm. Within the area of treatment, the intensity of the radiation dose is kept relatively uniform. Infrared wavelengths emitted from the bulb are typically filtered out before reaching the area of treatment as they can heat the skin, causing discomfort to the patient during the therapy. Further details of the apparatus used for phototherapeutic treatments can be found in Honigsmann et al., *Dermatology in General Medicines, 3rd ed*, T. B. Fitzpatrick et al., eds., 1728–1754, 1987.

When photosensitizing agents are used in combination with topically-applied sunscreens, the wavelength of the incident optical radiation must lie within the absorption spectrum of the photosensitizing agent. Depending on the drug used, this region is typically between 320–700 nm. Preferably, a laser, such as a tunable dye or solid-state laser, a metal vapor laser, or a diode laser, is used as the light source. Lasers are often the most practical light source for treatment because their high power output at the appropriate drug-activating wavelength can minimize exposure times. In addition, laser light can easily be coupled into flexible optical fibers to simplify the delivery of light to the treatment region. Other light sources, such as fluorescent bulbs and solar simulators (Dougherty, et al., *Cancer Res.* 38:2628–2635, 1978) may also be used.

Experimental Results

Variation with the Concentration of the Active Compound

The PPF provided by a sunscreen will vary with the concentration of the active compound. In order to determine the dependence of the PPF provided by DHA as a function of concentration, 6 patients having skin types ranging from I–IV were exposed to PUVA therapy featuring optical fluence levels high enough to cause erythema. Solutions containing 5%, 10% and 15% DHA (by weight) were used as photo-protectants for each patient, with a thin layer of solution at each concentration (0.2 cc/9 $cm^2$) applied to a different area of skin in each patient. The MPDs of the different areas were measured by exposing nine 1 $cm^2$ sites in a single skin area to incrementally increased doses of UVA radiation, with the radiation being centered near 365 nm. Comparison of the MPDs from these areas with the MPD from an area free of DHA allowed determination of the PPF, which could then be related to DHA concentration.

Figure 3:
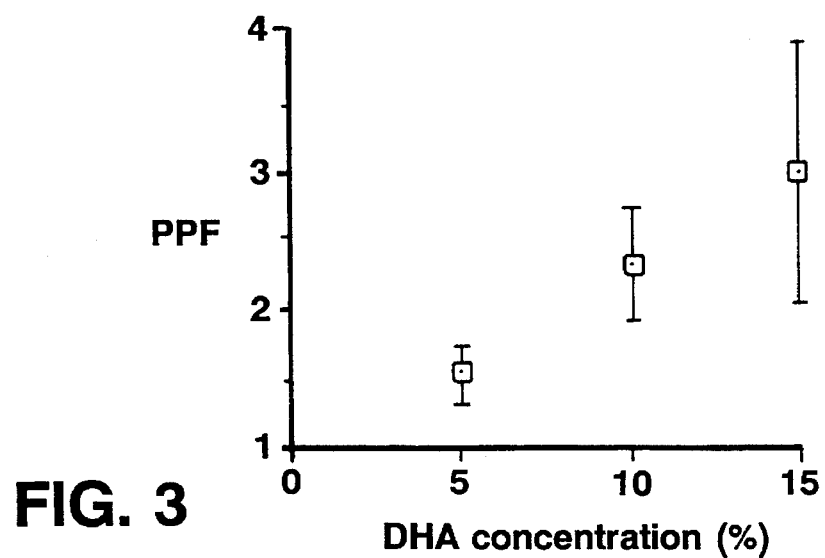
FIG. 3 shows a plot of the phototoxic protection factor (PPF) as a function of DHA concentration applied to human skin.

Referring to FIG. 3, the linear relationship between DHA concentration and PPF illustrates the increase in the protection against erythema provided by increasing concentrations of DHA. The rising slope of the data in the plot also indicates an absence of saturation occurring in the DHA absorption, suggesting that even higher concentrations of DHA may result in better protection against UVA wavelengths.

The PPF provided by DHA was also predicted using the non-invasive optical measurement described above. Experiments were conducted on two sunscreens by measuring the fluorescence excitation spectra of skin samples covered with a thin layer of sunscreen. Measurements were taken non-invasively by scanning the wavelength of an excitation light-source, followed by detection skin fluorescence at a single wavelength (Wan et al., *J. Photochem. Photobiol.* 34:493–499, 1981). The sunscreens used for experiments featured as an active compound either DHA or dansyl chloride, a fluorescent molecule commonly used in standard assays of corneocyte sloughing kinetics (Takahashi et al., *J. Soc. Cosmetic Chem.* 38:321–331, 1987; *Marks, Cutaneous Investigation in Health and Disease*, Leveque ed., Mercel Dekker, Paris, 33–47, 1989). A Spex fluorometer featuring an excitation light source and a monochrometer was fitted with an optical fiber bundle (Spex industries, Edison, N.J.) in order to deliver optical radiation to the sample of interest. Excitation wavelengths were chosen to match the peak of the absorption spectra of either DHA (350 nm) or dansyl chloride (335 nm). The excitation light was passed through the monochrometer (4 nm bandpass) and into one arm of the fiber bundle, and used to irradiate the skin. Fluorescence from the skin was collected by the same fiber and passed through an emission monochrometer (4 nm bandpass) and into a detector. Excitation spectra were measured at the peak of the emission spectrum of either DHA (500 nm) or dansyl chloride (465 nm), and were corrected for a weak background of auto-fluorescence due to emission from unstained skin. The same instrument was used to measure skin reflectance spectra by setting the excitation and emission monochrometers to the same wavelength. By comparing the incident optical intensity with induced fluorescence or reflected intensity, the optical density of the active compound at the absorbing wavelength was determined.

Figure 4:
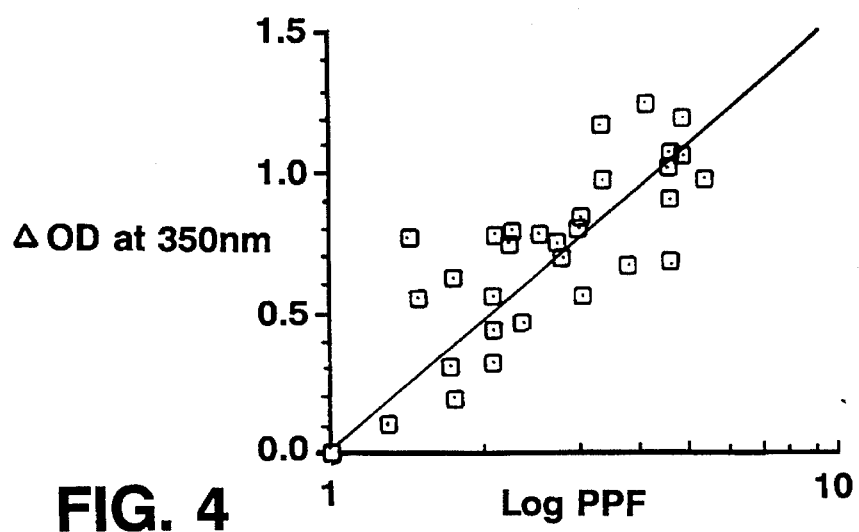
FIG. 4 is a graph showing the change in optical density at 350 nm for DHA stained skin samples plotted as a function of the PPF provided by DHA.

Referring now to FIG. 4, the change in OD, as defined in equation 3, was determined at 350 nm in various skin sites of living human volunteers stained with DHA, and is plotted as a function of the PPF. The PPF was determined by exposing the same skin sites to radiation at 350 nm after ingestion of 8-methoxypsoralen (8-MOP). The solid line in the graph is the fit of the data to equation 2. The agreement between the data and the fit indicates the ability of the skin reflectance method of the present invention to accurately predict the PPF provided by an applied sunscreen using a simple, non-invasive measurement.

Rapid Desquamation of the Skin

Figure 5:
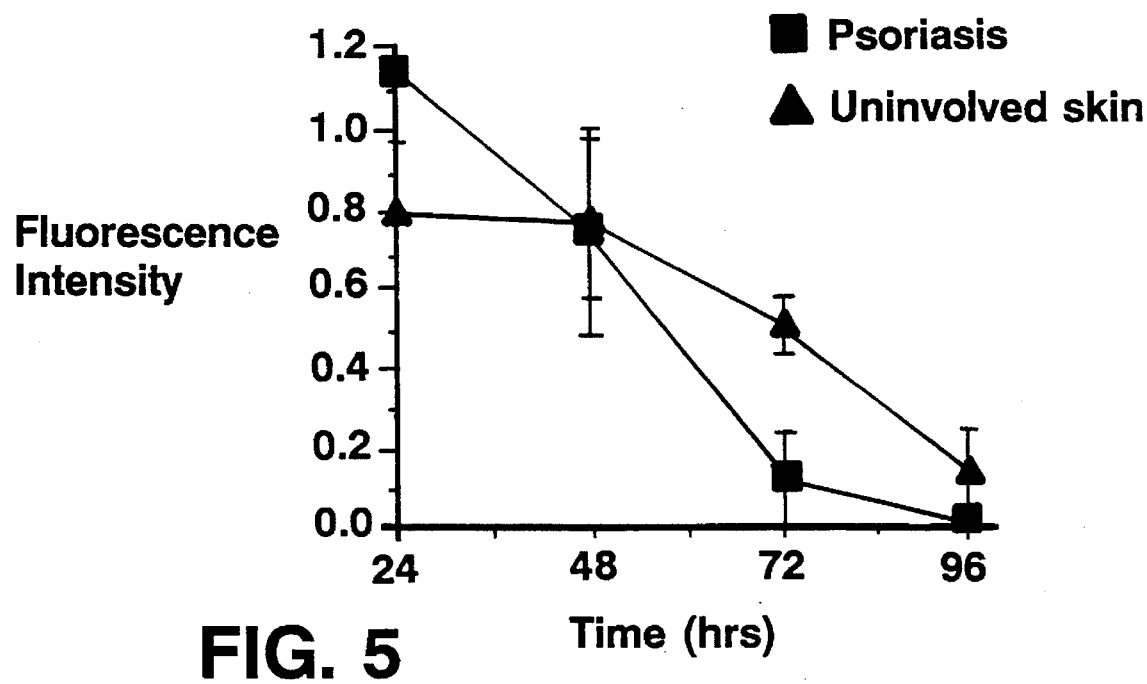
FIG. 5 is a graph showing the loss of fluorescence intensity as a function of time in psoriatic (squares) and normal (triangles) skin samples stained with DHA.
Figure 5A:
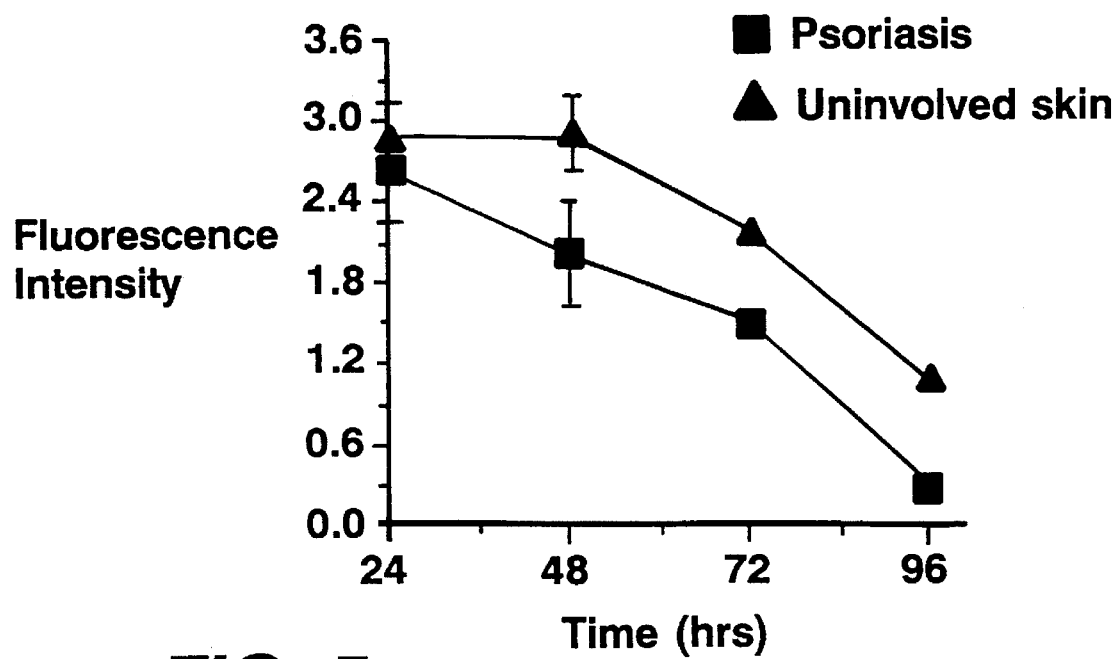
FIG. 5a is a graph showing the loss of fluorescence intensity as a function of time in psoriatic (squares) and normal (triangles) skin samples stained with dansyl chloride.

Stratum corneum sloughing was investigated by monitoring the time-dependent decrease in fluorescence intensity from the skin after topical application of a sunscreen. Referring now to FIGS. 5 and 5a, the time-dependent fluorescence intensities of psoriatic and non-affected skin samples stained with sunscreens including either DHA or dansyl chloride were compared. The induced fluorescence intensity is decreased faster from psoriatic plaques stained with DHA, with the DHA being completely shed from the skin approximately 96 hours after application. In contrast, the dansyl chloride stain takes a longer period of time to be shed from the psoriatic skin. The rapid decrease in the time-dependent fluorescence intensity induced in psoriatic skin stained with DHA implies a more superficial binding of DHA to the stratum corneum in comparison with dansyl chloride. Thus, DHA-containing sunscreens allow for effective phototherapeutic treatments to be carried out over a shorter time period, e.g., 72 hours after application.

Figure 6:
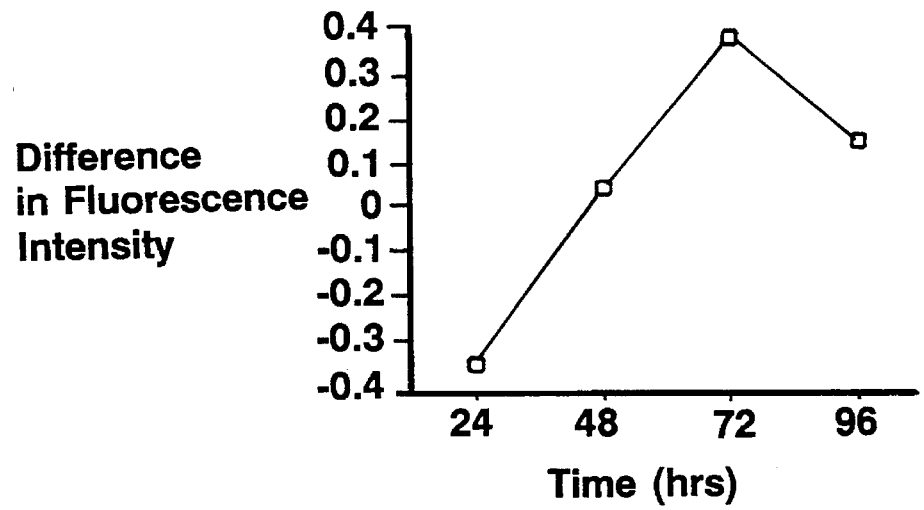
FIG. 6 is a graph showing the difference in fluorescence intensity between psoriatic and normal skin samples stained with DHA as a function of time.

Referring now to FIG. 6, the difference in induced fluorescence intensity between psoriatic and non-affected skin stained with DHA is shown to be greatest after 72 hours. The level of fluorescence intensity is directly correlated with the concentration of DHA bound to the skin sample. Thus, the peak in the data of FIG. 4 at 72 hours implies a time marking the maximum difference between the level of protection provided by DHA to psoriatic and non-affected skin. During a phototherapeutic treatment, an approximately 72-hour time period separating the application of DHA and exposure of the skin to optical radiation will result in the optimization of the conditions for phototherapy. The natural sloughing off process of the psoriatic tissue leaves affected regions with minimal DHA protection, while non-affected skin is relatively well protected from optical radiation. This allows higher optical fluences to be used during the phototherapy, thus accelerating the treatment of the psoriatic condition. It should be noted that active means for desquamating stratum corneum can be used to increase the rate at which sunscreens containing DHA or other active compounds are shed from the skin. In particular, alpha-hydroxy acids, such as lactic acid, are effective desquamating agents. When applied before, during, or after application of a highly-substantive sunscreen, the period of time required for loss of the sunscreen will be reduced. Physical means to remove the skin may also be used.

Use of DHA in Phototherapy

Figure 7:
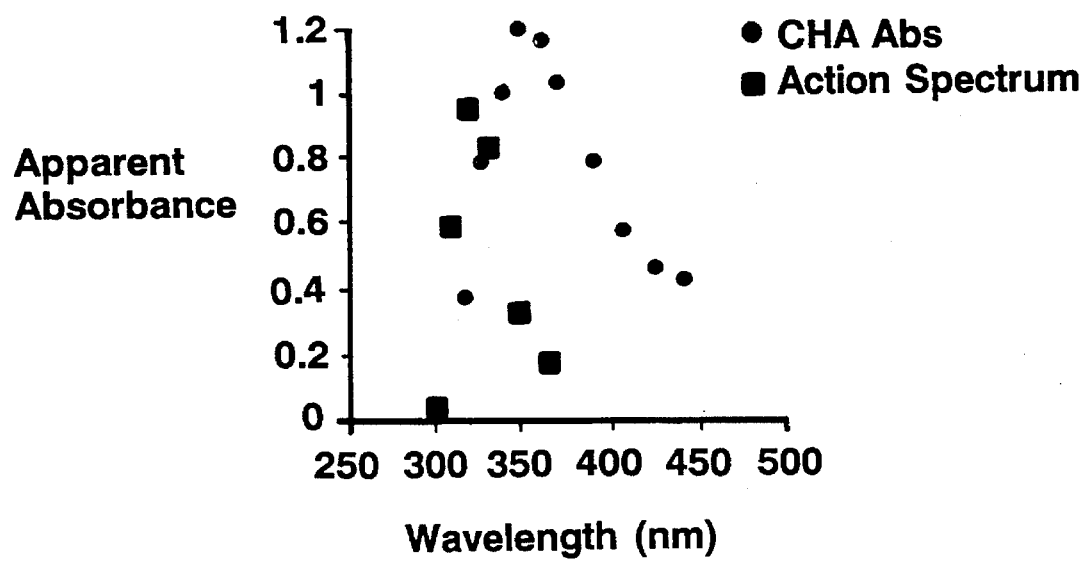
FIG. 7 is a graph showing the action spectrum of 8-MOP, which illustrates the effectiveness of each optical wavelength to produce erythema in psoralen sensitized skin samples. The graph also shows the absorption spectrum of DHA.

Referring now to FIG. 7, the absorption spectrum of DHA-stained skin extends from roughly 300–600 nm, and is peaked near 350 nm. The DHA staining is a yellow-brown or orange color, and is generally cosmetically acceptable because it mimics natural tanned skin. In FIG. 7, the absorption spectrum is plotted with the action spectrum of 8-MOP, which indicates the effectiveness of each wavelength of light to produce delayed erythema in psoralen-sensitized patients. Thus, during PUVA therapy, the skin is typically most sensitive to optical wavelengths near 320 to 330 nm. The overlap of the two spectra indicates that the active and most harmful optical wavelengths used in PUVA therapy will be preferentially absorbed by DHA. The absorption spectrum of other compounds listed in Table 1, in particular 2-Ethoxy-ethylhexyl-p-methoxycinnamate (cinnoxate), 2,2-Dihydroxy-4-methoxybenzophenone (dioxybenzone), 2-Hydroxy-4-methoxybenzophenone (oxybenzone), and 2-Hydroxy-4-methoxybenzophenone-5-sulfonic acid (sulisobenzone) are also peaked near 320 nm. Thus, these compounds will also function as particularly effective photo-protectants during UVA phototherapy.

Referring again to the DHA absorption spectrum plotted in FIG. 7, it is evident that conventional DHA preparations have poor absorbance in the UVB range (Levy, *J. Am. Acad. Dermatol.* 27:989–993, 1992). DHA absorbance is pH dependent, and a colored yellow product has been observed to appear at high, but still safe, pH levels in the human skin. This implies a shift in the absorption spectrum toward 300 nm for DHA incorporated in high pH environments. A high pH DHA preparation may therefore be used in a sunscreen as a UVB photo-protectant. An effective sunscreen for UVB phototherapy can also be made by using an increased concentration of DHA, resulting in a higher optical absorbance at wavelengths near 320 nm. Alternatively, active compounds such as Glyceryl-aminobenzoate, Amyl-p-dimethylamino benzoate (Padimate-A), 2-Ethyl-hexyl-p-dimethylamino benzoate (Padimate-O), and 3,3,5-Trimethylcyclohexyl-salicylate (homosalate), which are listed in Table 1, absorb light having wavelengths closer to the UVB range. These active compounds, when included in highly-substantive sunscreens, are useful photo-protectants.

Following administration of a photosensitizing agent, there is often appreciable uptake of the drug in the non-affected regions of skin, making it necessary to attenuate optical radiation incident on these regions during therapy. It is therefore desirable to use a sunscreen containing an active component having substantial optical absorption at the drug-activating wavelength of the light source. Referring again to FIG. 7, DHA-stained skin exhibits partial optical absorption between 320–600 nm, and thus can be used in combination with a variety of photosensitizing agents for treatment of affected regions of skin. Other active compounds partially absorbing light in this spectral regime could also be used as useful photo-protectants.

EXAMPLE 1

Phototherapeutic Treatment of Psoriasis Using Sunscreens Including DHA

With the information obtained from the above studies, aggressive PUVA therapy using sunscreens including DHA was initiated in twelve patients having chronic plaque psoriasis on greater than 30% of their body surfaces. The subjects had previously failed less aggressive therapies using topical corticosteroids or UVB radiation, and had received no treatments in the previous four weeks. PUVA therapy was administered according to standard protocol (Melski et al., *J. Invest. Dermatol.* 68:328, 1977). On one side of each patient, a solution containing 15% DHA was applied 72 hours before each treatment to allow for differential shedding of DHA from the psoriatic skin. During each visit, skin reflectance was measured in the DHA protected site, and the PPF was estimated. The light dosage applied to the DHA side was increased by a factor equivalent to the PPF value so that non-affected skin on each side of the patient was subjected to the same effective optical fluence. For example, if the dose without DHA was 4 J/cm$^2$, and the DHA provided a PPF=5 for the stained site, then a dose of 20 J/cm$^2$ was given to the skin stained with DHA. Because the skin on the DHA side is preferentially sloughed off in the psoriatic regions, these regions of psoriatic plaques were therefore subjected to a substantially higher dose of optical radiation. The Psoriasis Activity and Severity Index (PASI score) (Fredriksson et al., *U. Dermatologica* 157:238–244, 1978) was recorded weekly in order to follow the clinical response. The study endpoint was 90–100% clearance in all treated sites.

No phototoxic erythema was observed on the DHA side of patients completing the study, despite very high UVA doses of up to 25 J/cm$^2$ in a single treatment. PPF's as high as 10 were found with multiple repeated applications of DHA. All patients reported a persistent improvement in the psoriatic condition in the DHA treated site. In the first 5 patients, the mean number of treatments necessary for clearance of psoriasis was 12.4±5.77. These data, when compared to the unstained control skin necessitating 20–25 treatments for clearance of psoriasis, reflect the improvements of the method of the present invention (Melski et al., *J. Invest. Dermatol.* 68:328, 1977). It is apparent from PASI scores that the DHA treated sites cleared faster during the early weeks of treatment. After several treatments, it was noted that psoriatic skin began to retain the DHA longer than 3 days, producing unwanted UVA protection on the plaques due to a decrease in the epidermal turnover rate as the plaques began to heal.

The foregoing descriptions of the preferred method of the present invention has been presented for purposes of illustration and description. It is not intended to be exhaustive or to limit the invention to the precise form disclosed.

What is claimed is:

1. A method for treating a proliferative skin disorder in a human patient is needed thereof having affected and non-affected areas of skin, wherein said disorder results in said affected areas of skin being sloughed off at a greater rate than said non-affected areas of skin, said method comprising the steps of:

(a) topically applying to said affected and non-affected areas of skin a sunscreen providing photo-protection, (b) waiting for a time period sufficient for skin of said affected areas to be sloughed off to a greater degree than skin of said non-affected areas, and (c) exposing said affected and non-affected areas of skin of said patient to a selected level of optical radiation, said level of radiation being sufficient to treat said affected areas of skin and being insufficient to cause significant damage to said non-affected areas of skin.

2. The method of claim 1, wherein, between steps (b) and (c), the amount of photo-protection provided by said sunscreen to said affected and/or non-affected areas of skin is determined.

3. The method of claim 2, wherein said amount of photo-protection is determined by a non-invasive optical method involving measuring the reflectance properties of sunscreen-treated skin in said affected and/or non-affected areas.

4. The method of claim 1, wherein said sunscreen comprises an active compound which partially binds to portions of said skin.

5. The method of claim 4, wherein said active compound partially absorbs optical radiation having a wavelength between 290 and 400 nm.

6. The method of claim 5, wherein said active compound is DHA.

7. The method of claim 1, further comprising the step of administering to said patient prior to step (c) a compound selected from the group consisting of photosensitizing agents, psoralen, and psoralen-based compounds.

8. The method of claim 7, wherein said sunscreen comprises an active compound which partially binds to portions of said skin.

9. The method of claim 8, wherein said active compound partially absorbs optical radiation having a wavelength between 320 and 700 nm.

10. The method of claim 9, wherein said active compound is DHA.

11. The method of claim 1, wherein said proliferative skin disorder is any one of psoriasis, mycosis fungoides, eczema, actinic keratosis, or lichen planus.

12. The method of claim 1, wherein said time period is between 50 and 100 hours.

13. The method of claim 12, wherein said time period is about 72 hours.

14. The method of claim 1, wherein said selected level of optical radiation is between 1 and 50 J/cm$^2$.

15. The method of claim 4, wherein said active compound is present in a concentration by weight of between 1 and 15% said sunscreen.

* * * * *